(12) United States Patent
Betancourt Alexander

(10) Patent No.: US 11,130,799 B2
(45) Date of Patent: Sep. 28, 2021

(54) CARTILAGE REPLACEMENT COMPOSITIONS AND METHODS

(71) Applicant: Innovative Orthopedics, LLC, Chicago, IL (US)

(72) Inventor: Pablo Antonio Betancourt Alexander, Northbrook, IL (US)

(73) Assignee: INNOVATIVE ORTHOPEDICS, LLC, Chicago, IL (US)

(*) Notice: Subject to any disclaimer, the term of this patent is extended or adjusted under 35 U.S.C. 154(b) by 0 days.

(21) Appl. No.: 16/833,641

(22) Filed: Mar. 29, 2020

(65) Prior Publication Data

US 2020/0308254 A1   Oct. 1, 2020

Related U.S. Application Data

(60) Provisional application No. 62/826,819, filed on Mar. 29, 2019.

(51) Int. Cl.
| | | |
|---|---|---|
| *C07K 14/78* | (2006.01) |
| *A61L 27/24* | (2006.01) |
| *A61L 27/22* | (2006.01) |
| *A61K 9/00* | (2006.01) |

(52) U.S. Cl.
CPC .......... *C07K 14/78* (2013.01); *A61L 27/225* (2013.01); *A61L 27/24* (2013.01); *A61K 9/0019* (2013.01); *A61L 2430/06* (2013.01)

(58) Field of Classification Search
CPC ...... C07K 14/78; A61K 38/014; A61K 38/39; A61K 8/65
See application file for complete search history.

(56) References Cited

U.S. PATENT DOCUMENTS

| 2011/0182995 A1 | 7/2011 | Asgary |
| 2013/0296777 A1 | 11/2013 | Richards et al. |
| 2014/0356323 A1 | 12/2014 | Niklason et al. |
| 2015/0125537 A1 | 5/2015 | Goh et al. |
| 2015/0320904 A1 | 11/2015 | Yoo et al. |
| 2015/0367030 A1 | 12/2015 | Murray |
| 2016/0175489 A1 | 6/2016 | Babcock et al. |
| 2017/0348458 A1 | 12/2017 | Kesti et al. |
| 2018/0021138 A1 | 1/2018 | Estes et al. |
| 2018/0256309 A1 | 9/2018 | Shortkroff et al. |

FOREIGN PATENT DOCUMENTS

| CA | 2254350 A1 * | 5/2000 | ............. A61L 27/52 |
| CN | 1739797 A * | 3/2006 | |

OTHER PUBLICATIONS

Nunes de Barros et al. "A new heterologous fibrin sealant as a scaffold to cartilage repair—Experimental study and preliminary results", Experimental Biology and Medicine, 2016, pp. 1410-1415 (Year: 2016).*
Page et al., "The role of elastin-derived peptides in human physiology and diseases", Matrix Biology, 2019; 81-96 (Year: 2019).*
Verywell.com. obtained on Jan. 30, 2021; https://www.verywellhealth.com/calcium-gluconate-benefits-side-effects-dosage-and-interactions-4768506?print (Year: 2021).*
Reddy et al. "Bioactive oligopeptides in dermatology: Part I", Experimental Dermatology, 2012, 21, 563-568 (Year: 2012).*
Blanchevoye et al., "Interaction between the Elastin Peptide VGVAPG and Human Elastin Binding Protein," The Journal of Biological Chemistry, 2013, 288(2):1317-1328.
Robitzski, "Scientists say new artificial cartilage could be used in knees," NEOSCOPE, Jul. 6, 2020 <https://futurism.com/neoscope/artificial-cartilage-knees>.
International Search Report and Written Opinion for Application No. PCT/US2020/025611 dated Jul. 22, 2020 (13 pages).

* cited by examiner

*Primary Examiner* — Lianko G Garyu
(74) *Attorney, Agent, or Firm* — Michael Best & Friedrich LLP

(57) ABSTRACT

Described are compositions and methods for cartilage replacement. Also described are collagen scaffolds comprising the composition described herein.

15 Claims, 4 Drawing Sheets
(4 of 4 Drawing Sheet(s) Filed in Color)

Specification includes a Sequence Listing.

SEQUENCE LISTING

```
<160> NUMBER OF SEQ ID NOS: 2

<210> SEQ ID NO 1
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(4)
<223> OTHER INFORMATION: Xaa can be any naturally occurring amino acid

<400> SEQUENCE: 1

Xaa Gly Xaa Xaa Pro Gly
1               5
```

```
<210> SEQ ID NO 2
<211> LENGTH: 6
<212> TYPE: PRT
<213> ORGANISM: Artificial Sequence
<220> FEATURE:
<223> OTHER INFORMATION: Synthetic

<400> SEQUENCE: 2

Val Gly Val Ala Pro Gly
1               5
```

CARTILAGE REPLACEMENT COMPOSITIONS AND METHODS

CROSS-REFERENCE TO RELATED APPLICATIONS

This application claims priority to U.S. Provisional Patent Application No. 62/826,819, filed Mar. 29, 2019, which is incorporated herein by reference in its entirety.

SEQUENCE LISTING

The instant application contains a Sequence Listing which has been submitted electronically in ASCII format and is hereby incorporated by reference in its entirety. Said ASCII copy, created on May 19, 2020 is named "213474-9001-US02_SequenceListing.txt" and is 1 kb in size.

TECHNICAL FIELD

The present disclosure relates to compositions and methods for cartilage replacement.

BACKGROUND

While the body has efficient processes for healing and replacing most damaged tissue, the tissues in a joint often fail to heal and break down over the lifetime of an individual. In healthy individuals, the end of bones have a smooth surface made of cartilage. The cartilage is lubricated by a thin layer of synovial fluid allowing bones to slide smoothly against each other but also can prevent tissue healing. When the cartilage deteriorates or is injured, the joint becomes stiff and painful. One way to restore motion and reduce pain is through joint replacement surgery that replaces damaged bone with an artificial implant, usually of coated or uncoated metal or plastic. In addition to long recovery times and risk associated with any major invasive surgery, the artificial implants can be fraught by dislocation, fracturing, and erosion, which all end up resulting in additional surgical intervention.

A potential alternative to joint replacement exists through the insertion of new cartilage into the affected joint or a scaffold for generating new cartilage in situ. Chondrocytes, cartilage cells, can be reproduced in vitro, but placing the chondrocytes in a particular location and ensuring proliferation is challenging. In addition, injecting chondrocytes into a joint fails to recognize the fact that cartilage is more than just cells. Cartilage tissue is composed mostly of non-cellular material including water, collagen, and other extracellular matrix materials, most of which are produced and/or maintained by chondrocytes. Various scaffolds have been suggested to mimic the other components of cartilage including nanofibers, hydrogels, beads, mashes, and microspheres. The use of artificial compounds to form these scaffolds, however, pose their own clinical problems and adverse side effects. In addition, most of the currently used scaffolds do not address a mechanism to adhere the scaffold or replacement cartilage to the bone.

There remains a need, therefore, for compositions and methods for efficient, long-lasting, and minimally invasive cartilage replacement.

BRIEF SUMMARY

In one aspect, the disclosure provides compositions comprising collagen, an elastin peptide, and a divalent cation.

In another aspect, the disclosure provides a collagen scaffold. The collagen scaffold may comprise the composition as disclosed herein and a fibrin sealant. The disclosure also provides methods of making the collage scaffold described herein.

In another aspect, the disclosure provides a method for the replacement of damaged cartilage in a subject. The method may comprise removing damaged cartilage from the subject, preparing a composition as described herein, mixing the composition with a fibrin sealant to form a collagen scaffold, and injecting the collagen scaffold into the subject.

In another aspect, the disclosure also provides a kit. The kit comprises collagen, an elastin peptide, a divalent cation, and a fibrin sealant.

Other aspects and embodiments of the disclosure will become apparent in light of the following description and drawings.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1A shows the site of implantation as designated by the hashed circled area. FIG. 1B and FIG. 1C show images taken during implantation of the collagen scaffold compositions described herein. FIG. 1D shows the adhered collagen scaffold to the bone following implantation.

FIG. 2A and FIG. 2B show images taken during implantation of the control collagen scaffold. FIG. 2C shows the lack of the control collagen scaffold adhered to the bone following implantation.

DETAILED DESCRIPTION

Figure 1A:
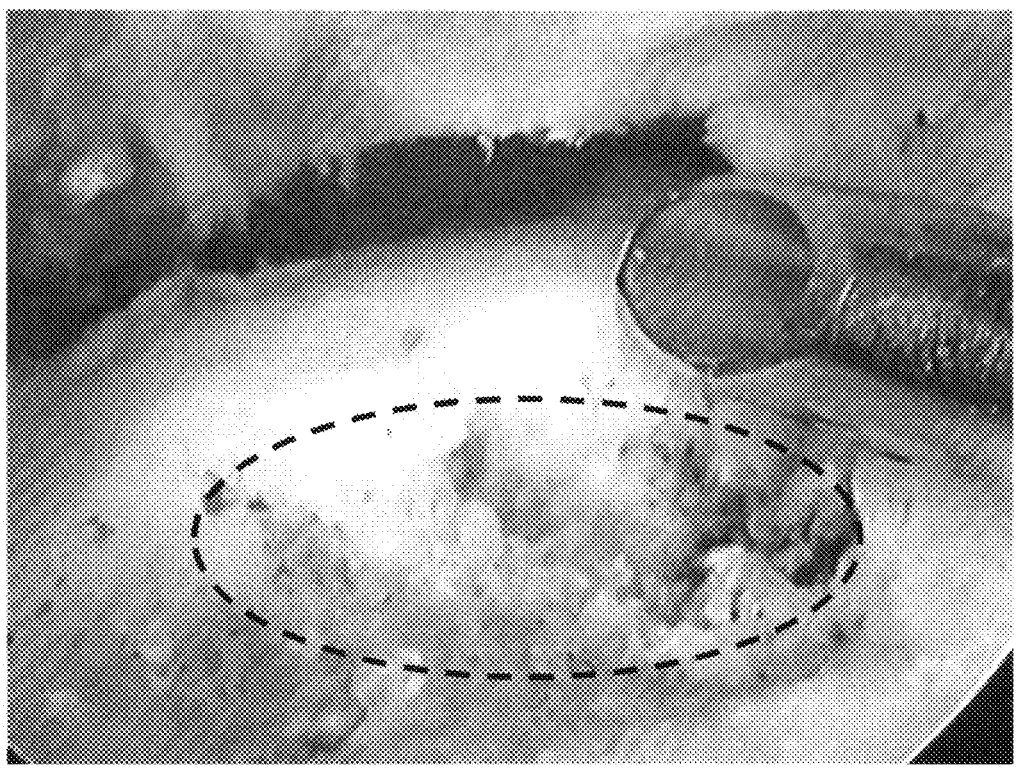
FIG. 1A, FIG. 1B, FIG. 1C, and FIG. 1D are images showing the implantation of the collagen scaffold compositions described herein.

The present disclosure provides compositions and methods for cartilage replacement. The composition has the ability to incorporate and nurture chondrocyte containing tissues while adhering to the bone. The composition includes collagen, an elastin peptide, and a divalent cation. The composition may be combined with a fibrin sealant or fibrin glue, to form a collagen scaffold for use in cartilage replacement methods.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification, and no structures shown in the drawings, should be construed as indicating that any non-claimed element is essential to the practice of the invention.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example, "about 1" may also mean from 0.5 to 1.4.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

As used herein, the terms "administering," "providing" and "introducing" are used interchangeably and refer to the placement of the compositions of the disclosure into a subject by a method or route that results in at least partial localization of the composition to a desired site. The compositions may be administered by any appropriate route that results in delivery to a desired location in the subject.

As used herein, the term "amino acid" refers to naturally occurring and non-natural synthetic amino acids as well as amino acid analogs and amino acid mimetics that function in a manner similar to the naturally occurring amino acids. Naturally occurring amino acids are those encoded by the genetic code. Amino acids can be referred to herein by either their commonly known three-letter symbols or by the one-letter symbols recommended by the IUPAC-IUB Biochemical Nomenclature Commission. Amino acids include the side chain and polypeptide backbone portions.

As used herein, the term "divalent cation" or "bivalent cation" are used to indicate a chemical element in which it has a positive charge state of two. For example, $Ca'$ is the divalent cation of calcium.

As used herein, the term "elastin peptide" in either singular or plural form refers to a peptide or amino acid sequence that corresponds to, is the biological equivalent of, is analogous with, or is substantially homologous with a portion of elastin but is not full-length elastin. The term "elastin peptide" is not meant to convey any meaning regarding the source or starting material or method of arriving at the elastin peptide.

As used herein, "fibrin sealant" or "fibrin glue" refers to a surgical formulation used to create a fibrin clot for hemostasis or wound healing. The sealants usually include fibrinogen and thrombin, which, when reconstituted in the presence of calcium chloride, convert the fibrinogen into fibrin monomers and give rise to a three-dimentional gel. Fibrin sealant preparations may also include additional components including aprotinin, fibronectin, and plasminogen. An example of a fibrin sealant includes Beriplast® P sealant from CSL Behring.

A "peptide" or "polypeptide" is a linked sequence of two or more amino acids linked by peptide bonds. The polypeptide may be natural, synthetic, or a modification or combination of natural and synthetic. Domains are portions of a polypeptide or protein that form a compact unit and are typically 15 to 350 amino acids long.

A "subject" or "patient" may be human or non-human and may include, for example, animal strains or species including those used as "model systems" for research purposes, such a mouse model as described herein. Likewise, patient may include either adults or juveniles (e.g., children). Moreover, patient may mean any living organism, preferably a mammal (e.g., human or non-human) that may benefit from the administration of compositions contemplated herein. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

2. Composition

The present disclosure provides a composition comprising collagen, an elastin peptide, and a divalent cation.

a. Collagen

The composition may comprise collagen. The collagen may be purified from a number of biological sources known in the art. For example, collagen proteins may be extracted from the connective tissues in the skin, bone, tendon, or other tissues of animals, including humans and bovines, as well as from fish skin and scale. Purified collagen may be further treated for sterilization. Alternatively, the collagen may be produced in vitro using well known molecular biology techniques. The collagen may have an amino acid sequence or a modified amino acid sequence of that found naturally in animals and fish.

The collagen may be any type of collagen. The collagen may be solubilized collagen. The collagen may form a fibrillar structure. The collagen may be Type 1, Type II, Type III, Type IV, Type V or a combination thereof. In some embodiments, the collagen is Type II collagen.

The composition may comprise about $1\times10^{-6}$ to about $10\times10^{-6}$ moles collagen. The composition may comprise at least $1\times10^{-6}$ moles, at least $2\times10^{-6}$ moles, at least $3\times10^{-6}$ moles, at least $4\times10^{-6}$ moles, at least $5\times10^{-6}$ moles, at least $6\times10^{-6}$ moles, at least $7\times10^{-6}$ moles, at least $8\times10^{-6}$ moles, or at least $9\times10^{-6}$ moles collagen. The composition may comprise less than $10\times10^{-6}$ moles, less than $9\times10^{-6}$ moles, less than $8\times10^{-6}$ moles, less than $7\times10^{-6}$ moles, less than $6\times10^{-6}$ moles, less than $5\times10^{-6}$ moles, less than $4\times10^{-6}$ moles, less than $3\times10^{-6}$ moles, or less than $2\times10^{-6}$ moles collagen. In some embodiments the composition comprises about $3\times10^{-6}$ moles collagen.

b. Elastin Peptide

The composition may comprise an elastin peptide. The elastin may be derived from sources known in the art. The elastin peptide may be isolated from an enzymatic digestion pool. The elastin peptide may be synthesized with a peptide sequencer. The molecular weight or length of the elastin peptide to be used in the present invention is not limited. The elastin peptide does not encompass, however, full-length elastin.

The elastin peptide may comprise an amino acid sequence of XGXXPG (SEQ ID NO: 1), wherein X is any amino acid. In some embodiments, the elastin peptide comprises an amino acid sequence of VGVAPG (SEQ ID NO: 2).

The composition may comprise about $1\times10^{-6}$ to about $10\times10^{-6}$ moles elastin peptide. The composition may comprise at least $1\times10^{-6}$ moles, at least $2\times10^{-6}$ moles, at least $3\times10^{-6}$ moles, at least $4\times10^{-6}$ moles, at least $5\times10^{-6}$ moles, at least $6\times10^{-6}$ moles, at least $7\times10^{-6}$ moles, at least $8\times10^{-6}$ moles, or at least $9\times10^{-6}$ moles elastin peptide. The composition may comprise less than $10\times10^{-6}$ moles, less than $9\times10^{-6}$ moles, less than $8\times10^{-6}$ moles, less than $7\times10^{-6}$ moles, less than $6\times10^{-6}$ moles, less than $5\times10^{-6}$ moles, less than $4\times10^{-6}$ moles, less than $3\times10^{-6}$ moles, or less than $2\times10^{-6}$ moles elastin peptide. In some embodiments, the composition comprises about $5\times10^{-6}$ moles elastin peptide.

The composition may comprise any absolute quantity of collagen and elastin peptide that results in a mole ratio of collagen to elastin peptide of about 1:1 to about 1:5. In some embodiments, the composition comprises a mole ratio of collagen to elastin peptide of about 1:1.6.

c. Divalent Cation

The composition may comprise a divalent cation. The divalent cation may be any cation with a positive two charge, for example, zinc, calcium, magnesium, manganese, iron, and copper. In preferred embodiments, the divalent cation is calcium, magnesium, or a combination thereof.

The divalent cation may comprise an organic or inorganic salt of the divalent cation. For example, the divalent cation may be joined with an organic or inorganic anion to form an organic or inorganic salt. The organic or inorganic salt may be a chloride salt, a carbonate salt, a gluconate salt, a phosphate salt, a sulphate salt, a bicarbonate salt, an acetate salt, a citrate salt, a silicate salt, a pyrophosphate salt, an oxide salt, an oxalate salt, a nitrite salt, a nitrate salt, a lactate salt, a hydroxide salt, a glucoheptonate salt, an ascorbate salt, or a combination or hydrate thereof. In exemplary embodiments, the divalent cation is calcium gluconate.

The composition may comprise about 0.5 to about 10 millimoles divalent cation. The composition may comprise at least 0.5 millimoles, at least 1 millimole, at least 2 millimoles, at least 3 millimoles, at least 4 millimoles, at least 5 millimoles, at least 6 millimoles, at least 7 millimoles, at least 8 millimoles, or at least 9 millimoles divalent cation. The composition may comprise less than 10 millimoles, less than 9 millimoles, less than 8 millimoles, less than 7 millimoles, less than 6 millimoles, less than 5 millimoles, less than 4 millimoles, less than 3 millimoles, less than 2 millimoles, or less than 1 millimole divalent cation. In some embodiments, the composition comprises about 7 millimoles divalent cation.

The composition may comprise any absolute quantity of collagen, elastin peptide, and divalent cation which results in a mole ratio of collagen to elastin peptide to divalent cation of about 1:1:1000 to about 1:5:4000. The composition may comprise a mole ratio of collagen to elastin peptide to divalent cation of about 1:1:2000, about 1:1:3000, about 1:1:4000, about 1:2:1000, about 1:2:2000, about 1:2:3000, about 1:2:4000, about 1:3:1000, about 1:3:2000, about 1:3:3000, about 1:3:4000, about 1:4:1000, about 1:4:2000, about 1:4:3000, about 1:4:4000, about 1:5:1000, about 1:5:2000, or about 1:5:3000. In some embodiments, the composition comprises a mole ratio of collagen to elastin peptide to divalent cation of about 1:1.6:2300.

The composition may further comprise a solvent. Suitable solvents include water, isotonic saline, or a buffer, for example, phosphate, Tris, HEPES, or other biologically suitable buffer.

The composition may incorporate therapeutic proteins including, but not limited to, hormones, cytokines, growth factors, clotting factors, anti-protease proteins (e.g., alphal-antitrypsin), angiogenic proteins (e.g., vascular endothelial growth factor, fibroblast growth factors), antiangiogenic proteins (e.g., endostatin, angiostatin), and other proteins that are present in the blood, bone morphogenic proteins (BMPs), osteoinductive factor (IFO), fibronectin (FN), endothelial cell growth factor (ECGF), cementum attachment extracts (CAE), ketanserin, human growth hormone (HGH), animal growth hormones, epidermal growth factor (EGF), interleukin-1 (IL-1), human alpha thrombin, transforming growth factor (TGF-beta), insulin-like growth factor (IGF-1), platelet derived growth factors (PDGF), fibroblast growth factors (FGFs), and periodontal ligament chemotactic factor (PDLGF), for therapeutic purposes.

3. Collagen Scaffold

The present disclosure provides a collagen scaffold comprising the compositions described herein and a fibrin sealant.

The fibrin sealant may be any fibrin sealant known in the art. Typically, a fibrin sealant is formed by enzymatic reactions involving fibrinogen and thrombin. The fibrin sealant may comprise a multi-component device, such that two supply reservoirs, or two syringes are used to keep the fibrinogen and thrombin separate until administration. The fibrin sealant may comprise a single-component device.

The present disclosure also provides a method of making a collagen scaffold, comprising preparing a composition as described herein and mixing the composition with a fibrin sealant. The compositions described herein may be mixed with all or part of the fibrin sealant. For example, if a multi-component device for the fibrin sealant is used, the composition may be mixed with one or both of the fibrinogen and thrombin before administration.

The collagen scaffold may additionally serve as a base to add elements that can help repair cartilage damage. For example, these elements may include cellular components, including but not limited to, progenitor cells, chondrocytes, either autologous, homologous, or heterologous or non-cellular components, such as endosomes, exosomes, vacuoles or any other element useful in the repair of cartilage lesions.

4. Methods of Use

The present disclosure also provides a method for the replacement of damaged cartilage in a subject. The method comprises: removing damaged cartilage from the subject, preparing a composition as described herein, mixing the composition with a fibrin sealant to form a collagen scaffold, and injecting the collagen scaffold into the subject to replace the damaged cartilage.

Removing the damaged cartilage also includes locating and identifying damaged cartilage in the subject. This may be done, for example, with magnetic resonance imaging. The cartilage may be removed by any well-known method in the art. The surgeon can recognize the best and most applicable method to use based on the size and location of the damaged cartilage. The surgery may involve a standard synovectomy, bursectomy, or capsulotomy. The cartilage may be removed by the use of shavers, basket tweezers, or chondrotomic or other suitable devices.

If the underlying bone does not have a normal surface, bone formation within the cartilage, endostosis, or new bone on the surface of the bone, exostosis, has to be removed and repaired with osseous matrix prior to injection of the collagen scaffold.

Following mixing the compositions described herein with the fibrin sealant to form a collagen scaffold, the collagen scaffold is injected into the area in which the damaged cartilage was removed. The injection may be completed in the absence of water.

The collagen scaffolds described herein may be used alone or in combination with other three-dimensional (3-D) scaffolds or other traditional repair devices or techniques.

5. Kit

The present disclosure additionally provides kits comprising:
(a) collagen;
(b) an elastin peptide;
(c) a divalent cation; and
(d) a fibrin sealant.

In some embodiments, the collagen, the elastin peptide, and the divalent cation are co-formulated. In some embodiments, the collagen, the elastin peptide, and the divalent cation are co-formulated with the fibrin sealant. In some embodiments, the collagen, the elastin peptide, and the divalent cation, and the fibrin sealant are co-packaged.

The kits can also comprise compounds and/or products co-packaged, co-formulated, and/or co-delivered with other components. For example, a drug manufacturer, a physician, or a hospital can provide a kit comprising those components listed above and another component for delivery to a patient.

The disclosed kits can be employed in connection with disclosed methods.

The kits may further include information, instructions, or both on how the kit can be used to repair damaged cartilage. The information and instructions may be in the form of words, pictures, both, or the like.

6. Examples

It will be readily apparent to those skilled in the art that other suitable modifications and adaptations of the methods of the present disclosure described herein are readily applicable and appreciable and may be made using suitable equivalents without departing from the scope of the present disclosure or the aspects and embodiments disclosed herein. Having now described the present disclosure in detail, the disclosure will be more clearly understood by reference to the following examples, which are merely intended only to illustrate some aspects and embodiments of the disclosure, and should not be viewed as limiting to the scope of the disclosure. The disclosures of all journal references, U.S. patents, and publications referred to herein are hereby incorporated by reference in their entireties.

Example 1. Preparation of the Composition 0.5 mLs of a solution containing elastin peptide at 10.6 mM (Grupo Proteo) was mixed with 2 mLs of bovine Type 2 collagen 1.5 mM and 0.5 mLs calcium gluconate (PiSA® Farmaceutica) at a concentration of 14 M in an appropriate solvent.

The elastin peptide was hydrolyzed peptides of the full-length elastin protein, with an average molecular weight of 7000 Daltons. The average molecular weight was used to calculate the concentration recited above.

By nature, Type 2 collagen is usually hydrophilic and fails to work in a scaffold. When mixed with the elastin peptide and divalent cation, however, it was surprisingly found that the type II collagen takes on a hydrophobic nature. This surprising hydrophobicity made the composition appropriate for population with chondrocytes and/or chondrocyte containing tissues.

Example 2. Preparation of the Collagen Scaffold

In addition to hydrophobic type 2 collagen, elastin peptide and calcium gluconate, the scaffold contains a fibrin sealant. An example of the invention used the commercially available Beriplast® P sealant. The Beriplast® P is a two-component sealant in which one syringe contains 2 mL of a solution of fibrinogen and aprotinin and a second syringe with a solution of calcium chloride and thrombin. The composition was mixed with the thrombin solution of the second syringe. In addition, a fibrin sealant can be used that does not include aprotinin. Omitting aprotinin from the fibrin sealant can improve the strength of the scaffold.

Example 3. Cartilage Replacement

The formulated scaffold as described in Example 2 was used for a cartilage replacement surgery. The damaged cartilage was located by means of CartiloGram magnetic resonance imaging. Two portals in the skin were opened by way of an ordinary arthroscopic surgery. Further imaging of the cartilage damage was observed after insertion of a trocar with a camera through one of the portals.

An initial standard synovectomy, bursectomy, or capsulotomy was completed and the damaged cartilage, which is relatively softer than the normal cartilage, was removed by shavers, backet tweezers, and/or chondrotomic devices. The removal of the damaged cartilage was verified by a stylus hook and touch. In some instances, thermal radio frequency was also used to define the edge between normal and damaged cartilage.

After confirmation that the bone had a normal surface, the fibrin sealant was mixed with the composition as described in Example 2 to form the collage scaffold and injected into the lesion. A hook stylus was used to help the scaffold stick to the bone in regular form. During the injection of the scaffold, the flow of water was stopped for ten seconds. After two minutes, the behavior of the solidified scaffold was checked by observing joint movement.

Figure 1B:
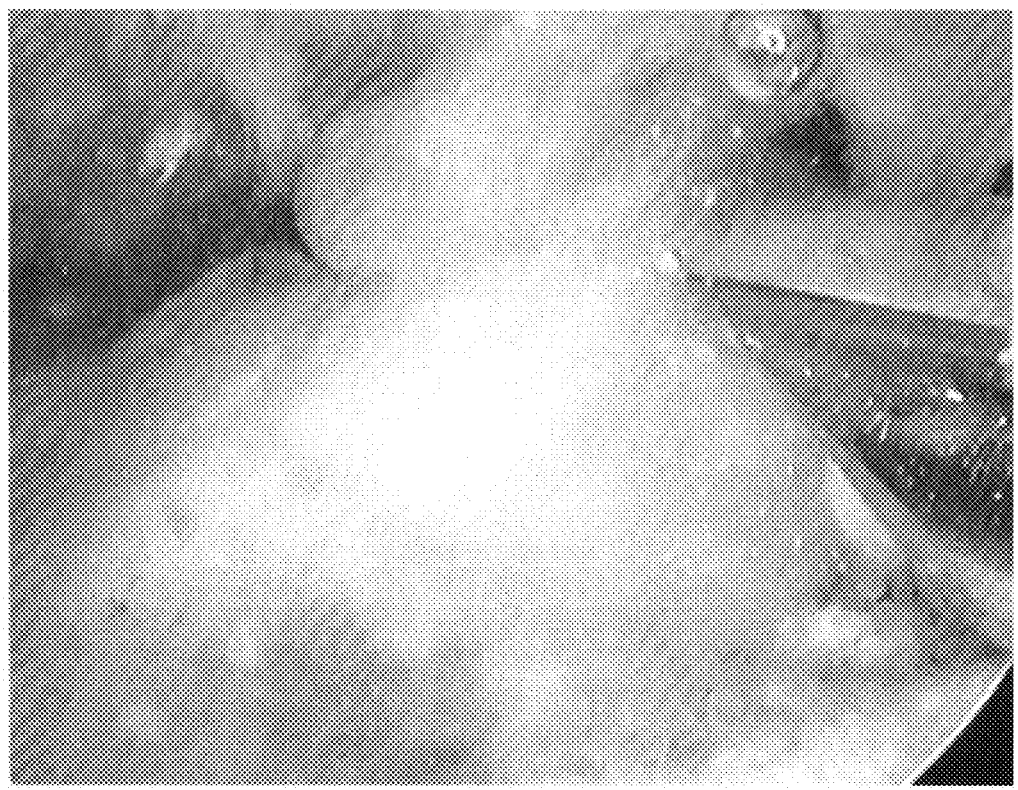
Figure 1C:
Figure 1D:
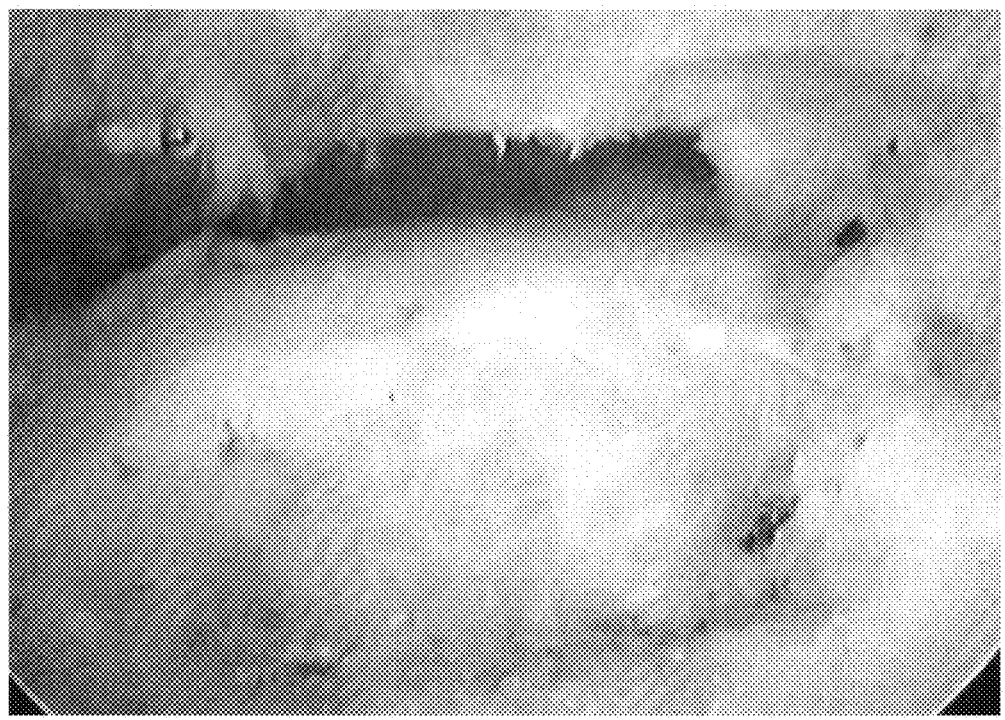

The use of the material was also tested in a porcine model, as shown in FIGS. 1A-1D. A site for implantation was designated (FIG. 1A, hashed circle). During implantation of the material described herein, the material was injected and remained near the site for implantation (FIG. 1B). Following injection, a hook stylus was used to shape the scaffold around the site of implantation (FIG. 1C). As shown in FIG. 1D, the scaffold adhered to the bone in the site of implantation and formed a regular scaffold structure.

Figure 2A:
FIG. 2A, FIG. 2B, and FIG. 2C are images showing the implantation of a control collagen scaffold composition comprising type II collagen without the elastin peptide or calcium gluconate.
Figure 2B:
Figure 2C:
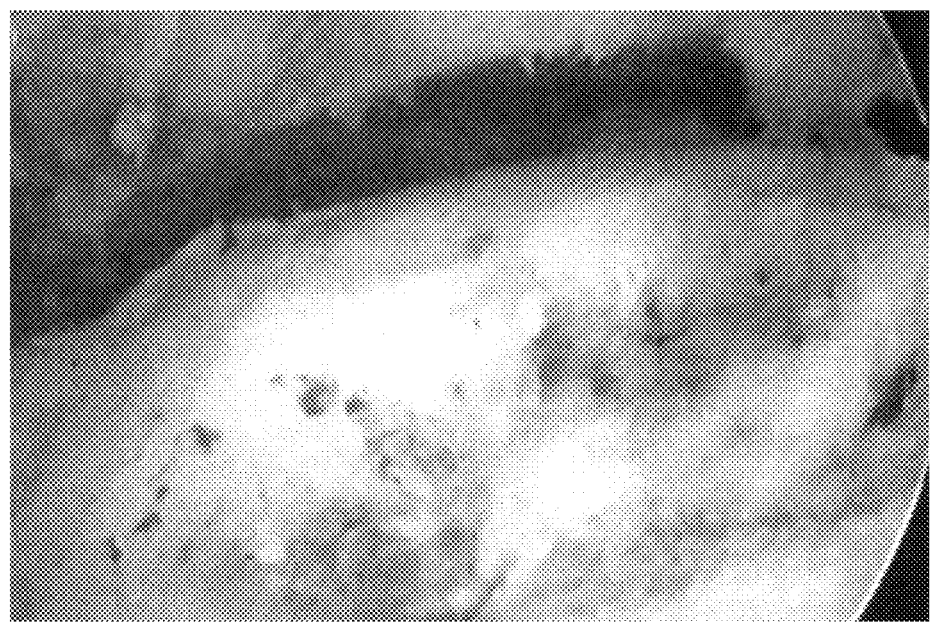

For comparison, a control scaffold only containing type II collagen without the elastin peptide or the calcium gluconate was also prepared and tested in the porcine model (FIGS. 2A-2C). During implantation, the control scaffold did not remain near the site for implantation and was unable to adhere to the bone throughout the process (FIG. 2A and FIG. 2B). As shown in FIG. 2C, following injection, only a small amount of the control scaffold remained at the site of implantation. Even that small amount was unable to effectively adhere to the bone.

The scaffold compositions described herein are able to be easily implanted using standard orthoscopic techniques and implements. Contrary to the control scaffold, the scaffold compositions described herein produced a scaffold which showed hydrophobic characteristics such that when injected it did not diffuse away from the site of implantation. In addition, the scaffold composition showed a superior ability to adhere to the bone at the site of implantation and offer a more stable, longer lasting scaffold for cartilage repair.

For reasons of completeness, various aspects of the invention are set out in the following numbered clauses:

Clause 1. A composition comprising collagen, an elastin peptide, and a divalent cation.

Clause 2. The composition of clause 1, wherein the collagen is type 2 collagen.

Clause 3. The composition of clause 1 or clause 2, wherein the composition comprises about $1 \times 10^{-6}$ to about $10 \times 10^{-6}$ moles collagen.

Clause 4. The composition of any of clauses 1-3, wherein the composition comprises about $3 \times 10^{-6}$ moles collagen.

Clause 5. The composition of any of clauses 1-4, wherein the elastin peptide comprises an amino acid sequence of XGXXPG (SEQ ID NO: 1), wherein X is any amino acid.

Clause 6. The composition of any of clauses 1-5, wherein the elastin peptide comprises an amino acid sequence of VGVAPG (SEQ ID NO: 2).

Clause 7. The composition of any of clauses 1-6, wherein the composition comprises about $1 \times 10^{-6}$ to about $10 \times 10^{-6}$ moles elastin peptide.

Clause 8. The composition of any of clauses 1-7, wherein the composition comprises about $5 \times 10^{-6}$ moles elastin peptide.

Clause 9. The composition of any of clauses 1-8, wherein the composition comprises a mole ratio of collagen to elastin peptide of about 1:1 to about 1:5.

Clause 10. The composition of any of clauses 1-9, wherein the divalent cation is magnesium or calcium.

Clause 11. The composition of any of clauses 1-10, wherein the divalent cation comprises an organic or inorganic salt.

Clause 12. The composition of any of clauses 1-11, wherein the organic or inorganic salt is a chloride salt, a carbonate salt, a gluconate salt, a phosphate salt, a sulphate salt, a bicarbonate salt, an acetate salt, a citrate salt, a silicate salt, a pyrophosphate salt, an oxide salt, an oxalate salt, a nitrite salt, a nitrate salt, a lactate salt, a hydroxide salt, a glucoheptonate salt, an ascorbate salt, or a combination or hydrate thereof.

Clause 13. The composition of any of clauses 1-12, wherein the divalent cation is calcium gluconate.

Clause 14. The composition of any of clauses 1-13, wherein the composition comprises about 0.5 to about 10 millimoles divalent cation.

Clause 15. The composition of any of clauses 1-14, wherein the composition comprises about 7 millimoles divalent cation.

Clause 16. The composition of any of clauses 1-15, wherein the composition comprises a mole ratio of collagen to elastin peptide to divalent cation of about 1:1:1000 to about 1:5:4000.

Clause 17. A collagen scaffold comprising: the composition of any of clauses 1-16 and a fibrin sealant.

Clause 18. A method of making a collagen scaffold, comprising: preparing a composition of any of clauses 1-16 and mixing the composition with a fibrin sealant.

Clause 19. A method for the replacement of damaged cartilage in a subject in need thereof, comprising: removing damaged cartilage from the subject; preparing a composition of any of clauses 1-16; mixing the composition with a fibrin sealant to form a collagen scaffold; and injecting the collagen scaffold into the subject to replace the damaged cartilage.

Clause 20. A kit comprising: collagen; an elastin peptide; a divalent cation; and a fibrin sealant.

The invention claimed is:

1. A composition comprising:
   collagen type II;
   an elastin peptide; and
   calcium gluconate.

2. The composition of claim 1, wherein the composition comprises about $1 \times 10^{-6}$ to about $10 \times 10^{-6}$ moles of collagen type II.

3. The composition of claim 1, wherein the composition comprises about $3 \times 10^{-6}$ moles of collagen type II.

4. The composition of claim 1, wherein the elastin peptide comprises an amino acid sequence of XGXXPG (SEQ ID NO: 1), wherein X is any amino acid.

5. The composition of claim 1, wherein the elastin peptide comprises an amino acid sequence of VGVAPG (SEQ ID NO: 2).

6. The composition of claim 1, wherein the composition comprises about $1 \times 10^{-6}$ to about $10 \times 10^{-6}$ moles elastin peptide.

7. The composition of claim 6, wherein the composition comprises about $5 \times 10^{-6}$ moles elastin peptide.

8. The composition of claim 1, wherein the composition comprises a mole ratio of collagen type II to elastin peptide of about 1:1 to about 1:5.

9. The composition of claim 1, wherein the composition comprises about 0.5 to about 10 millimoles of calcium gluconate.

10. The composition of claim 9, wherein the composition comprises about 7 millimoles of calcium gluconate.

11. The composition of claim 1, wherein the composition comprises a mole ratio of collagen type II to elastin peptide to calcium gluconate of about 1:1:1000 to about 1:5:4000.

12. A collagen scaffold comprising:
    the composition of claim 1 and
    a fibrin sealant.

13. A kit comprising:
    collagen type II;
    an elastin peptide;
    calcium gluconate; and
    a fibrin sealant.

14. A method of making a collagen scaffold, comprising:
    preparing the composition of claim 1, and
    mixing the composition with a fibrin sealant to produce a collagen scaffold.

15. A method for the replacement of damaged cartilage in a subject in need thereof, comprising:
    removing damaged cartilage from the subject;
    mixing the composition of claim 1 with a fibrin sealant to form a collagen scaffold; and
    administering the collagen scaffold into the subject to replace the damaged cartilage.

* * * * *